United States Patent
Utku (10) Patent No.: US 10,806,745 B2
(45) Date of Patent: *Oct. 20, 2020

(54) ANALOGUES OF ETOPOSIDE FOR THE TREATMENT OF TUMOURS

(71) Applicant: Purdue Pharma L.P., Stamford, CT (US)

(72) Inventor: Nalan Utku, Bonn (DE)

(73) Assignee: Purdue Pharma L.P.

( * ) Notice: Subject to any disclaimer, the term of this patent is extended or adjusted under 35 U.S.C. 154(b) by 59 days.

This patent is subject to a terminal disclaimer.

(21) Appl. No.: 15/865,818

(22) Filed: Jan. 9, 2018

(65) Prior Publication Data

US 2018/0125873 A1 May 10, 2018

Related U.S. Application Data

(63) Continuation of application No. 13/641,557, filed as application No. PCT/EP2010/003118 on May 20, 2010, now Pat. No. 9,889,147.

(30) Foreign Application Priority Data

Apr. 16, 2010 (WO) ................ PCT/EP2010/002347
Apr. 20, 2010 (WO) ................ PCT/EP2010/002409

(51) Int. Cl.

| A61K 31/7048 | (2006.01) |
|---|---|
| A61K 31/704 | (2006.01) |
| A61K 45/06 | (2006.01) |
| C07H 17/04 | (2006.01) |

(52) U.S. Cl.
CPC ........ *A61K 31/7048* (2013.01); *A61K 31/704* (2013.01); *A61K 45/06* (2013.01); *C07H 17/04* (2013.01)

(58) Field of Classification Search
None
See application file for complete search history.

(56) References Cited

U.S. PATENT DOCUMENTS

| 2006/0293254 A1 | 12/2006 | Gaedicke et al. |
| 2008/0274910 A1 | 11/2008 | Utku |
| 2009/0175879 A1 | 7/2009 | Utku |
| 2011/0183921 A1 | 7/2011 | Utku |

FOREIGN PATENT DOCUMENTS

| WO | 03048166 A1 | 6/2003 | | |
| WO | WO-03048166 A1 * | 6/2003 | ........... | C07D 493/04 |

OTHER PUBLICATIONS

Ajani et al., Cancer J Sci Am., 1999, 5(2), pp. 112-114. (Year: 1999).*
Ajani, J. A. et al., "Oral etoposide for patients with metastatic gastric adenocarcinoma." Cancer J. Sci. Am., 1999,5 (2): 112-114.
Lange, B. S., "Charakterisierung eines neuen hydrolytisch aktivierbaren Prodrugs von Etoposid und seine Wirksamkeit bei "Multidrug" Resistenz und beim Neuroblastom." Department of Medicine-Charite-University Medicine Berlin, 2006, Doctoral Thesis.
Lange, B. S. et al., "Rationally Designed Hydrolytically Activated Etoposide Prodrugs, A Novel Strategy for the Treatment of Neuroblastoma." Cancer Letters, 2003, 197, 225-230.
Schroeder, U. et al., "Hydrolytically activated etoposide prodrugs inhibit MDR-1 funtion and eradicate established MDR-1 multidrug-resistant T-cell leukemia." Blood, Jul. 2003, 102 (1): 246-253.
Wrasidlo, W. et al., "Synthesis, Hydrolytic Activation and Cytotoxicity of Etoposide Prodrugs." J. Bioorg. Med. Chem. Lett., 2002, 12: 557-560.
Xu, G. et al., "Human Carboxylesterase 2 is Commonly Expressed in Tumor Tissue and is Correlated with Activation of Irinotecan." Clinical Cancer Research, Aug. 2002, 8: 2605-2611.

* cited by examiner

*Primary Examiner* — Traviss C McIntosh, III
(74) *Attorney, Agent, or Firm* — McCarter & English, LLP; Yu Lu; Wei Song (57) ABSTRACT

Compounds for treatment of a patient having a tumour that is metastatic and/or that reduces an organ function, wherein the compounds are of the general formula:

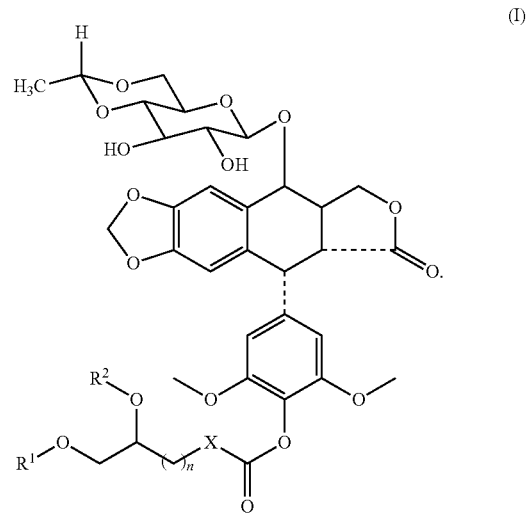

(I)

wherein X is O, NH and S, wherein n is 0, 1 or 2, wherein $R^1$ and $R^2$ are H, methyl or ethyl, or together form a group $CR^3R^4$, and wherein $R^3$ and $R^4$ are H, methyl or ethyl.

12 Claims, 3 Drawing Sheets

ANALOGUES OF ETOPOSIDE FOR THE TREATMENT OF TUMOURS

CROSS-REFERENCE TO RELATED APPLICATIONS

This application is a continuation application of co-pending application Ser. No. 13/641,557, filed Dec. 28, 2012; which is the U.S. National Stage of International Application No. PCT/EP2010/003118, filed May 20, 2010; and which claims priority to International Application PCT/EP2010/002347, filed Apr. 16, 2010; and International Application PCT/EP2010/002409, filed Apr. 20, 2010.

BACKGROUND OF THE INVENTION

The present invention relates to analogues of etoposide for the treatment of patients having a tumour, more particularly a tumour that is metastatic and/or that reduces an organ function. The invention also relates to an in vitro method of selecting a respective patient for treatment with an analogue of etoposide.

Etoposide is a chemotherapeutic drug derived from podophyllotoxin and acts as an inhibitor of topoisomerase II. The enzyme topoisomerase II induces transient DNA double strand breaks to enable modifications of DNA tertiary structure. Etoposide acts as a topoisomerase II poison leading to a stabilization of the cleavable complex, resulting in multiple non-repairable double strand breaks.

There are two isoforms of topoisomerase II, alpha and beta. Expression of topoisomerase II alpha is regulated with the cell cycle, with a gradual increase starting in the G1 phase that peaks in G2/M, whereas in quiescent cells or terminally differentiated cells topoisomerase II is extremely underregulated. The action of etoposide is cell cycle dependent with maximal activity during the G2-S phase.

Etoposide is an important anti-tumour drug and is commonly used against a number of diverse tumours, for example paediatric cancers including lymphatic lymphomas, rhabdomyosarcomas and neuroblastomas. Etoposide is also used in the treatment of many common cancers in adults. It is the first line therapy in a series of tumours, e.g. small cell lung cancer, diffuse large cell lymphoma, testicular germ cell tumour (testicular cancer) and Hodgkin lymphoma. Etoposide is also active in e.g. Non-Hodgkin lymphoma, AIDS-related Kaposi's sarcoma, bladder cancer, Ewing sarcoma, brain tumours and ovarian germ cell tumours. However, there are factors limiting the applicability of etoposide, such as poor water solubility, metabolic inactivation, toxicity with side effects such as leucopenia and neutropenia and the resistance against etoposide developing in the treated patients.

In cancer therapy, the chances of successful treatment and the prognosis of a tumour patient are highly dependent on the type and the localisation of the tumour. Metastatic tumours are tumours that have spread from their respective organ of origin to a different part of the body. The survival rate and the chances of successful treatment often depend on whether or not a tumour is local or has metastasised.

Metastasis occurs when tumour cells break away from a primary tumour and spread to other parts of the body via the blood and/or the lymphatic system, are deposited within normal tissue and finally proliferate to form a metastasis. Metastasis requires invasive growth of a tumour, that is, growth into the surrounding structures. Invasive growth often leads to a breach of the barrier to the blood and/or lymph vessels.

Metastases are a hallmark of malignancy. They are common in advanced or late-stage cancer. In order to be able to metastasise, malignant cells must be able to break away from the primary tumour and to degrade the extracellular matrix that separates the tumour from the surrounding normal tissue. Metastasising tumours have acquired additional mutations or capabilities as compared to non-metastasising tumours. This includes the ability to overcome the body's metastasis-preventing mechanisms, which for example involve metastasis suppressor proteins. The metastatic potential of tumour cells depends on the ability to breach body barriers like the base membrane, to actively migrate to a blood and/or lymph vessel, to invade the vessel and to exit it, to withstand attacks by the immune system during the migration in the body, and to proliferate and form a new tumour. Metastatic potential is a characteristic of malignant cancer cells and depends on individual genetic features of the tumour.

Metastasis is involved in most deaths from cancer. The ability of a tumour to form metastases (e.g. in advanced or end-stage cancer), makes the chances of successful treatment of the tumour patient drop considerably. In contrast to treatment of a non-metastasising tumour, after a tumour has metastasised, treatment of the patient often fails. Accordingly, initial success in the treatment of a patient having a non-metastasising tumour with a particular drug—let alone the mere successful completion of pre-clinical studies with the drug—does not predict success in treatment with the drug of a tumour that has formed metastases (a tumour that is metastatic). Thus, even though there are a number of treatment options for primary tumours, there remains a need for medicaments able to act efficiently on the more aggressive metastatic tumours.

Often organ function is reduced due to the presence of a tumour in the organ. Usually, invasive tumour growth as defined above is responsible for the reduction in organ function, if the tumour growth interferes with the physiological function of the organ, e.g. by destroying the morphological and/or physiological integrity. Examples are advanced or late-stage tumours. There is a need to provide compounds showing a therapeutic effect also on such (more aggressive) tumours. Again, whether a compound can be successfully used to treat such a tumour cannot be predicted from success of the compound in pre-clinical studies or in the treatment of tumours that do not reduce an organ function.

An important issue in the chemotherapy of tumours, which occurs in the case of many chemotherapeutic agents (including etoposide) is that a large number of patients initially respond to treatment but after a while lose sensitivity to the agent. This phenomenon is called resistance.

It is often mediated by expression of the MDR-1 gene which confers to the cells a multidrug-resistant phenotype. Expression of MDR-1 is e.g. observed in the resistance to etoposide and other naturally derived topoisomerase II inhibitors like anthracyclines and mitoxantrone. Multidrug-resistant cell clones are able to survive and proliferate despite the presence of cytotoxic agents (chemotherapeutic agents, chemotherapeutic drugs). The MDR-1 (multidrug resistance-1) gene encodes a protein called P-glycoprotein (permeability glycoprotein), an ABC-transporter. Expression of MDR-1 is linked to a poor prognosis.

Resistance against chemotherapeutic agents may also be mediated by other mechanisms, like down-regulation of pro-apoptotic mechanisms or up-regulation of anti-apoptotic mechanisms, increased metabolisation of the agent or down-regulation of its target (which is topoisomerase II in the case of etoposide).

WO 03/048166 A1 discloses a class of podophyllotoxins used for example for the treatment of tumour patients and the synthesis of these podophyllotoxins. The treatment of tumours that are metastatic or that reduce an organ function is not disclosed.

SUMMARY OF THE INVENTION

It has been an object of the present invention to provide an option for the treatment of a patient having a tumour that is metastatic and/or that reduces an organ function.

It has surprisingly been found that this object is solved by a compound of formula (I)

(I)

wherein X is selected from the group consisting of O, NH and S, n is 0, 1 or 2, and R and $R^2$ are independently selected from the group consisting of H, methyl and ethyl, or together form a group $CR^3R^4$ wherein $R^3$ and $R^4$ are independently selected from the group consisting of H, methyl and ethyl, for the treatment of a patient having a tumour that is metastatic and/or that reduces an organ function.

It is additionally advantageous to provide a compound that is able to overcome a multidrug-resistant phenotype mediated by MDR-1 or a resistance to treatment with certain chemotherapeutic agents.

It is also desirable to provide a compound that is effective at a low dose.

The compounds according to formula (I) are chemotherapeutic drugs. They are chemical modifications of etoposide (analogues of etoposide) differing in that a water-soluble ester group is attached to etoposide.

It has now been found that compounds according to formula (I) are effective on metastatic tumours and/or tumours reducing an organ function. Patients that had an advanced cancer or an end-stage cancer responded to treatment with the compounds. Compounds of formula (I) have shown to be effective against progressive tumours. It was possible to achieve a therapeutic success even in patients in which other therapeutic options had failed.

The term "metastasis" as used in this application includes local, regional and distant metastases. Local metastases are formed in the vicinity of the primary tumour, usually when malignant tumour cells are leak into the respective tissue, also across organ borders. Regional metastases are metastases present in draining lymph nodes, which are usually formed when tumour cells leak into the lymph vessels and localise in the respective lymph nodes (localised spread to regional lymph nodes near the primary tumour). Distant metastases are often formed when tumour cells leak into blood vessels; they are localised in organs distant from the organ of the primary tumour.

The feature that a tumour reduces an organ function means that due to the presence of the tumour, the physiological function of a respective organ (for example its metabolic, structural, regulatory or protective function) is impaired as compared to the respective healthy organ that does not carry a tumour. Preferred examples of such organs are the bones, brain, liver, lungs and lymph nodes.

The compounds of formula (I) have an enhanced therapeutic profile as compared to etoposide, including higher cytotoxicity and efficacy on tumours, even in etoposide-resistant in vitro- and in vivo-models and in multidrug-resistant tumours.

The synthesis of compounds of formula (I) has been reported before and may be accomplished according to WO 03/048166 A1 and Wrasidlo et al. (2002) Bioorg Med Chem Lett 12, 557-560, the relevant portions of which are hereby incorporated by reference.

It has been shown before that compounds of formula (I), for instance a compound in which X=O, n=1 and $R^1=R^2=H$ (which is called CAP7.1), are up to 1000 times more potent than etoposide, e.g. in terms of cytotoxicity on tumour cells (see e.g. WO 03/048166 A1).

According to the invention, in formula (I), X is preferably O. Preferably, n is 1. $R^1$ and $R^2$ are preferably independently of each other H or form a group $CR^3R^4$. Preferably, $R^3$ and/or $R^4$ are methyl. It is preferred that $R^1$ and $R^2$ are identical and/or that $R^3$ and $R^4$ are identical.

In a preferred embodiment, the tumour is cancer.

Preferably, the compound of formula (I) is selected from the group consisting of (CAP7.1)

and

-continued (pro-CAP7.1)

Preferably, the patient is a human patient.

The compounds of formula (I) as defined above are particularly suitable for treating drug-resistant (e.g. etoposide-resistant) tumours, especially multidrug-resistant tumours and thus are able to overcome drug (e.g. etoposide) resistance and particularly multidrug resistance. Thus, a preferred embodiment relates to a compound of formula (I) as defined above for the treatment of a patient having a tumour that is metastatic and/or that reduces an organ function, wherein the tumour has a multidrug-resistant phenotype that is mediated by MDR-1. This means that MDR-1 is expressed to such an extent that the tumour or certain cells of the tumour display(s) a multidrug-resistant phenotype, i.e. the response to certain drugs (compounds, chemotherapeutic agents) is impaired.

An expression level of MDR-1 is preferably higher in a tumour cell than in a corresponding average non-tumour cell.

The cytotoxic effect of the compounds of formula (I) on tumours, including multidrug-resistant tumours, is illustrated in Table 1, which gives examples of tumour cells sensitive to CAP7.1 treatment. This effect is observed in vitro and in vivo. The according in vitro assays (e.g. activity against leukaemia and cancer cell lines, effect on multidrug-resistant cells, in vivo toxicity and efficacy in a multidrug-resistant T-cell leukaemia xenograft model) are performed according to known protocols, e.g. those disclosed in WO 03/048166 A1.

TABLE 1

Tumour cell lines sensitive to treatment with CAP7.1 are shown. The tissue of origin is indicated. A plus ("+") sign in the column "resistance" indicates that the respective cell line is multidrug-resistant due to MDR-1 (MDR-1 resistant).

| Cell line | Tissue | Resistance |
|---|---|---|
| Jurkat | T lymphocyte, acute T cell leukaemia | |
| Raji | B lymphoblast, Burkitt's lymphoma | |
| RL | B lymphoblast, non-Hodgkin lymphoma | |
| U-937 | macrophage, histiocyte, histiocyt. lymphoma | + |
| Reh | pre-B-acute lymphoblastic leukemia | |
| HT-29 | colorectal adenocarcinoma | |
| SW480 | colon adenocarcinoma | + |
| A2780 | ovarian carcinoma | |
| Kelly | neuroblastoma | + |
| H69 | small cell lung carcinoma | + |
| HVP69 | small cell lung carcinoma | + |

Preferably, the tumour is resistant to treatment with a therapeutic protein or a compound selected from the group consisting of chemotherapeutic drugs other than the compounds of formula (I) as defined above, that is, treatment with such a protein or chemotherapeutic drug has failed. Respective proteins are preferably selected from the group consisting of therapeutic antibodies and kinases, and respective chemotherapeutic drugs are preferably selected form the group consisting of alkylating agents, platinum-based agents, intercalating agents, antibiotics, inhibitors of mitosis, taxanes, inhibitors of topoisomerase and antimetabolites. In particular, the chemotherapeutic drug is selected from the group consisting of all-trans retinoic acid, azacitide, azathioprine, bleomycin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, mechlorethamine, mercaptopurine, methotrexate, mitoxantrone, oxaliplatin, paclitaxel, pemetrexed, teniposide, tioguanine, trofosfamide, valrubicin, vinblastine, vincristine, vindesine and vinorelbine.

Preferably, the tumour is a solid tumour, in particular a solid cancer.

In a preferred embodiment, the tumour is selected from the group consisting of adenocarcinoma (e.g. colon adenocarcinoma and colorectal adenocarcinoma), hypopharynx cancer (e.g. squamous cell hypopharynx cancer, especially with pulmonary metastases), lung cancer (e.g. lung carcinoma, small cell lung cancer and squamous cell cancer of the lung), diffuse large cell lymphoma, Burkitt's lymphoma, Hodgkin lymphoma, Non-Hodgkin lymphoma, histiocytic lymphoma, lymphatic lymphoma, acute T-cell leukaemia, pre-B-acute lymphoblastic leukaemia, gall bladder cancer (e.g. adenocarcinoma of the gall bladder, especially with lymph node metastases), bile duct carcinoma, thymus carcinoma (e.g. sarcomatoid thymus carcinoma, especially with pulmonary metastases), urothelium carcinoma, testicular cancer (e.g. testicular germ cell tumour, seminoma and non-seminoma, especially with renal, pulmonary, retroperitoneal, hepatic and/or cerebral metastases), prostate cancer, bladder cancer, brain tumour, AIDS-related Kaposi's sarcoma, Ewing sarcoma, rhabdomyosarcoma, neuroblastoma (in particular paediatric neuroblastoma, especially advanced paediatric neuroblastoma), ovarian cancer (e.g. ovarian germ cell tumour, ovarian carcinoma or adenous carcinoma, especially with abdominal metastases), breast cancer and cancer of unknown primary origin (CUP syndrome, e.g. small-cell metastases—especially in the brain—with unknown primary tumour).

A preferred treatment is a treatment that leads to a stagnation of tumour growth or a remission of the tumour.

Preferably, the treatment is at a daily dose of the compound of formula (I) of 350 mg/m² or below. It has surprisingly been shown that the compounds of formula (I) due to their efficiency are active already in low concentrations, so that the daily dose can be lower than a corresponding dose of etoposide. More preferably, the daily dose of a compound of formula (I) is 250 mg/m$^2$ or below, even more preferably 150 mg/m$^2$ or below, still more preferably 100 mg/m$^2$ or below and most preferably 50 mg/m$^2$ or below.

In a preferred embodiment, the treatment comprises a first period of administration of a compound a formula (I) on a number of consecutive days (for example 4, 5, 6 or 7 days), followed by an intermittent period in which no compound of formula (I) is administered (the intermittent period lasting for example 1 to 4 weeks), followed by a second period of administration of a compound a formula (I) on a number of consecutive days (for example 4, 5, 6 or 7 days). Preferably, the first period of administration is 5 days, the second period of administration is 5 days and/or the intermittent period is 2 to 3 weeks.

Preferably, the treatment involves single dosage unit per day.

The compounds of formula (I) are preferably administered by intravenous infusion.

It has now been found that the compounds of formula (I) are enzymatically converted to the chemotherapeutic drug etoposide by carboxylesterases, in particular human carboxylesterases and especially CES1 and CES2. Carboxylesterases are present in a subset of tumours. For example, the publication Xu et al. (2002) Clinical Cancer Research 8, 2605-2611 shows that CES2 is expressed in 66% of the analysed human tumours (101 of 154), whereas it is expressed in 92% (55 of 60) of normal tissues.

It has been found that in mice with high levels of the corresponding carboxylesterases, the half life of CAP7.1 is very short (less than 5 minutes), whereas in primates it is longer and in humans it is 15-30 minutes. The fact that CAP7.1 shows activity in mice in a xenograft model of MDR tumours suggests that CAP7.1 distributes early to the tumour sites.

With respect to the fact that carboxylesterases cleave the compounds of formula (I) to etoposide, the compounds of formula (I) can be regarded as prodrugs.

However, the compounds of formula (I) also have effects that are independent of their conversion to etoposide. Thus, they have a profile that can be differentiated from etoposide. For example, the compounds of formula (I) directly inhibit the MDR-1 gene product P-glycoprotein, in contrast to etoposide, which is ineffective on P-glycoprotein.

Thus, P-glycoprotein-mediated substrate efflux is reduced, which contributes to the effectiveness of the compounds of formula (I) on multidrug-resistant tumours and to the effect of overcoming multidrug resistance. Compounds of formula (I), e.g. CAP7.1, are not a substrate for P-glycoprotein. Etoposide is pumped out of the cells, whereas in contrast, compounds of formula (I), e.g. CAP7.1, remain in the cells for a longer period. This is indicative of the compounds of formula (I) inhibiting the activity of the pump (through direct binding to P-glycoprotein or mediated by binding to another protein). Thus, the concentration of the compounds of formula (I) inside tumour cells is higher than the concentration of etoposide. Compounds of formula (I) do not show cross-resistance with etoposide. In addition, the compounds of formula (I) remaining in the cells are able—in contrast to etoposide—to induce an arrest in the G2 phase of the cell cycle, and to lead to a delayed effect (delayed induction of apoptosis) as compared to etoposide. Measurements have shown that cells exit the G2 phase after at a later stage, at which apoptosis is induced. In the case of etoposide, apoptosis is complete after 48 h, as compared to 120 h in the case of CAP7.1 (a compound of formula (I)).

This delayed apoptosis is likely a reason for a better tolerability and/or safety in the administration of the compounds of formula (I), in particular CAP7.1, as compared to etoposide, because an acutely toxic peak is avoided. Compounds of formula (I), particularly CAP7.1, have been shown to cause fewer side effects than etoposide in preclinical and clinical studies.

The compounds of formula (I) are effective in the inhibition of topoisomerase II. They inhibit topoisomerase II enzymes including topoisomerase II α and topoisomerase II β at the transcriptional level.

In a preferred embodiment, the present invention relates to a compound of formula (I) as defined above for the treatment of a patient having a tumour that is metastatic and/or that reduces an organ function, wherein the tumour expresses CES1 and/or CES2. Preferably, in this embodiment the fraction of tumour cells that express CES1 and/or CES2 is 50% or higher, more preferably 75% or higher.

According to a preferred embodiment, the present invention relates to a compound of formula (I) as defined above, wherein the treatment is a combination therapy together with a second drug. The second drug is preferably a protein or a chemotherapeutic drug. The combination therapy preferably involves the simultaneous or sequential administration of the compound of formula (I) and the second drug.

The second drug is preferably selected from the group consisting of therapeutic antibodies, kinases, alkylating agents, platinum-based agents, intercalating agents, antibiotics, inhibitors of mitosis, taxanes, inhibitors of topoisomerase and antimetabolites. A preferred second drug is selected from the group consisting of all-trans retinoic acid, azacitide, azathioprine, bleomycin, carboplatin, capecitabine, cisplatin, chlorambucil, cyclophosphamide, cytarabine, daunorubicin, docetaxel, doxifluridine, doxorubicin, epirubicin, epothilone, fluorouracil, gemcitabine, hydroxyurea, idarubicin, imatinib, mechlorethamine, mercaptopurine, methotrexate, mitoxantrone, oxaliplatin, paclitaxel, pemetrexed, teniposide, tioguanine, trofosfamide, valrubicin, vinblastine, vincristine, vindesine and vinorelbine. Particularly preferred is carboplatin.

Preferred tumours in the case of a combination therapy are selected from the group consisting of adenocarcinoma (e.g. colon adenocarcinoma and colorectal adenocarcinoma), hypopharynx cancer (e.g. squamous cell hypopharynx cancer, especially with pulmonary metastases), lung cancer (e.g. lung carcinoma, small cell lung cancer and squamous cell cancer of the lung), diffuse large cell lymphoma, Burkitt's lymphoma, Hodgkin lymphoma, Non-Hodgkin lymphoma, histiocytic lymphoma, lymphatic lymphoma, acute T-cell leukaemia, pre-B-acute lymphoblastic leukaemia, gall bladder cancer (e.g. adenocarcinoma of the gall bladder, especially with lymph node metastases), bile duct carcinoma, thymus carcinoma (e.g. sarcomatoid thymus carcinoma, especially with pulmonary metastases), urothelium carcinoma, testicular cancer (e.g. testicular germ cell tumour, seminoma and non-seminoma, especially with renal, pulmonary, retroperitoneal, hepatic and/or cerebral metastases), prostate cancer, bladder cancer, brain tumour, AIDS-related Kaposi's sarcoma, Ewing sarcoma, rhabdomyosarcoma, neuroblastoma, ovarian cancer (e.g. ovarian germ cell tumour, ovarian carcinoma or adenous carcinoma, especially with abdominal metastases), breast cancer and cancer of unknown primary origin (CUP syndrome, e.g. small-cell metastases—especially in the brain—with unknown primary tumour). Neuroblastoma (in particular paediatric neuroblastoma, especially advanced paediatric neuroblastoma) is particularly preferred.

Particularly preferred is a combination therapy that leads to a synergistic enhancement of efficacy.

Another aspect of the present invention relates to a pharmaceutical composition comprising a compound of formula (I) as defined above and a second drug. The above statements regarding the second drug apply accordingly. The pharmaceutical composition preferably additionally comprises a carrier and/or an excipient.

According to another aspect, the present invention relates to an in vitro-method of selecting a patient having a tumour that is metastatic and/or that reduces an organ function for treatment with a compound of formula (I), comprising the steps of (a) testing a sample from the tumour for expression of CES1 and/or CES2, and (b) selecting the patient if CES1 and/or CES2 is expressed.

A preferred method comprises as step (b) selecting the patient if the fraction of tumour cells that express CES1 and/or CES2 is 50% or higher, preferably 75% or higher.

According to an alternative aspect, the present invention relates to a compound of formula (I) as defined above for the treatment of a patient having a tumour that expresses CES1 and/or CES2. Corresponding to this aspect, the present invention also relates to an in vitro-method of selecting a patient having a tumour for treatment with a compound of formula (I) as defined above, comprising the steps of (a) testing a sample from the tumour for expression of CES1 and/or CES2, and (b) selecting the patient if CES1 and/or CES2 is expressed.

DETAILED DESCRIPTION OF PREFERRED EMBODIMENTS

In various investigations (cellular assays, animal models, human clinical studies), the compounds of formula (I) and in particular CAP7.1 show a unique therapeutic profile within the class of topoisomerase inhibitors: a better efficacy (even at low doses) in comparison to some other chemotherapeutic drugs (especially etoposide), an efficacy also in tumours resistant to other therapies and in particular etoposide-resistant tumours (examples are hypopharynx cancer, gall bladder cancer, ovarian cancer, testis cancer (testicular cancer), thymus carcinoma, cancer of unknown primary origin (CUP) and neuroblastoma), an efficacy in advanced cancer patients at a low dose, a better tolerability/fewer side effects (even at a higher dose) in comparison to some other chemotherapeutic drugs and a prevention of an immediate increase of etoposide concentration through slow conversion of the compounds of formula (I).

EXAMPLES

Example 1: Conversion of CAP7.1 to Etoposide by Carboxylesterases

The time-dependent conversion of CAP7.1 to etoposide by different carboxylesterases and foetal calf serum was analysed by incubating CAP7.1 with CES1, CES2 and CES3, respectively. 5 µM CAP7.1 was pre-incubated for 3 min in 999 µl 0.1 mol/l sodium phosphate ($NaH_2PO_4$, Roth, Karlsruhe, Germany) pH 7.4 at 37° C. After that, CES1, CES2 and CES3, respectively, were added. Controls were incubated with 10% foetal calf serum (FCS, positive control) or in buffer (negative control). At different time points, aliquots were subjected to HPLC in order to analyse the formed products.

Figure 1:
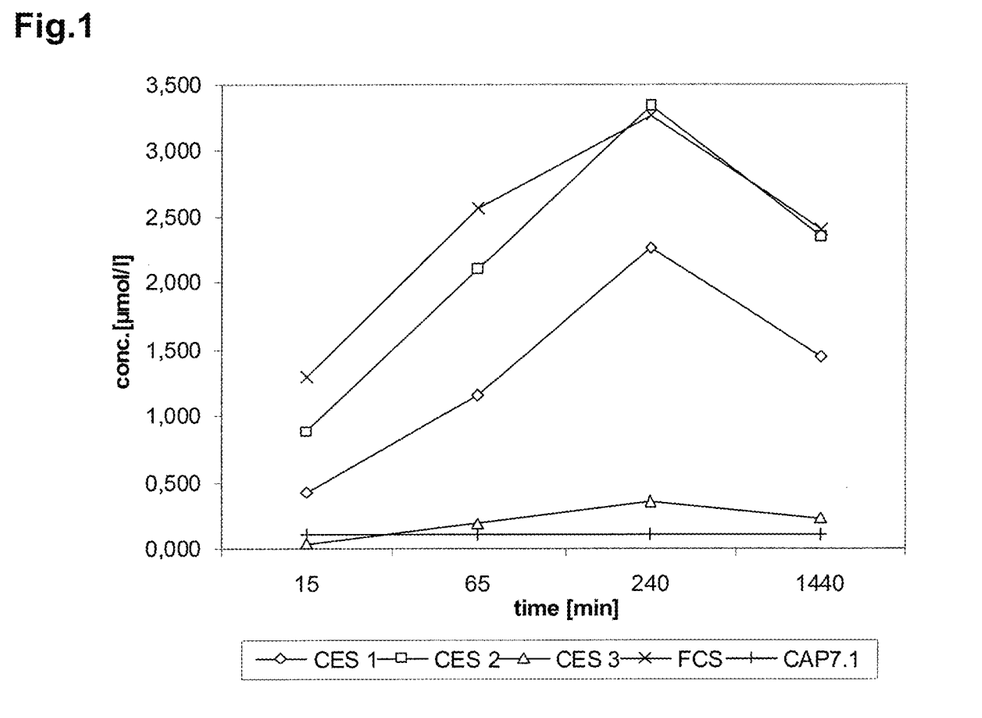
FIG. 1 shows the time-dependent conversion of CAP7.1 to etoposide by different carboxylesterases and by foetal calf serum.

In FIG. 1, the levels of the etoposide formed are depicted. CES2 (square symbols) cleaves CAP7.1 as efficiently as the positive control FCS (X symbols). CES1 (diamond symbols) also efficiently cleaves CAP7.1, whereas in the case of CES3 (triangle symbols), substantially no cleavage of CAP7.1 is observed. The negative control (cross symbols) shows that CAP7.1 is stable under the chosen conditions.

Example 2: Inhibition of Topoisomerases II at the Transcriptional Level by CAP7.1 and by Etoposide U937 cells grown in RPMI 1640/DMEM medium supplemented with 10% foetal bovine serum, 2 mmol/l L-glutamine and 100 U/ml/100 µg/ml Penicillin/Streptomycin were washed and resuspended at a concentration of $10^6$ cells/well into 6-well plates in solutions containing $10^{-4}$ mol/l CAP7.1 and $10^{-4}$ mol/l etoposide, respectively. One of the controls involved the treatment of the cells with 0.05% (1 µl) DMSO. Untreated cells are also shown as a control.

After an incubation time of 24 h, expression was analysed by determining mRNA levels by real-time PCR. In the respective lanes of FIG. 2, the bands for topoisomerase II α (322 bp), topoisomerase II β (304 bp) and the GAPDH control (358 bp) are shown. In the $H_2O$ control lane, showing the results of the $H_2O$ control sample, no bands were observed.

Figure 2:
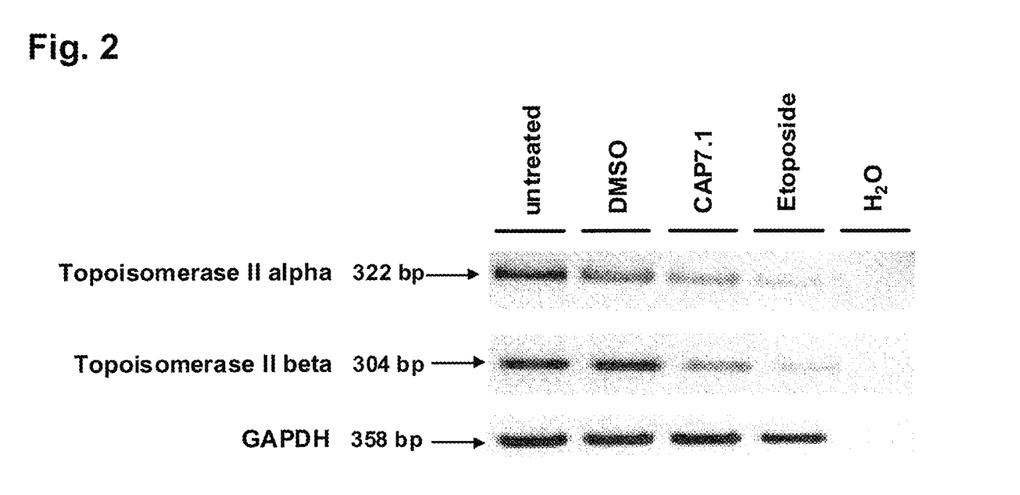
FIG. 2 shows the inhibition of topoisomerase II proteins in U937 cells by CAP7.1 and by etoposide at the transcriptional level.

Untreated cells expressed both topoisomerase II α and β at a strong level. Both CAP7.1 and etoposide lead to a significant decrease of expression of both topoisomerase II α and β.

Example 3: Inhibition of MDR-1 Activity by CAP7.1

By means of an assay using JC-1, MDR-1 activity was assessed in Kelly cells, which express MDR-1. JC-1 is a cationic staining dye which is taken up by living cells. JC-1 is recognized by the MDR-1 gene product (P-glycoprotein) and pumped to the outside of the cell (substrate efflux). Thus, MDR-1 activity is indicated by a reduction in intracellular JC-1 signal.

Kelly cells grown in RPMI medium were washed and resuspended at a concentration of 10 cells/ml in solutions containing JC-1 in a final concentration of 50 nmol/l. Cells were incubated for 15 min in the presence of $10^{-4}$ mol/l CAP7.1 and $10^{-4}$ mol/l etoposide, respectively. The control contained 1 µl (0.05%) DMSO. Cells were analysed for JC-1 staining in a FACScanto II flow cytometer.

Figure 3:
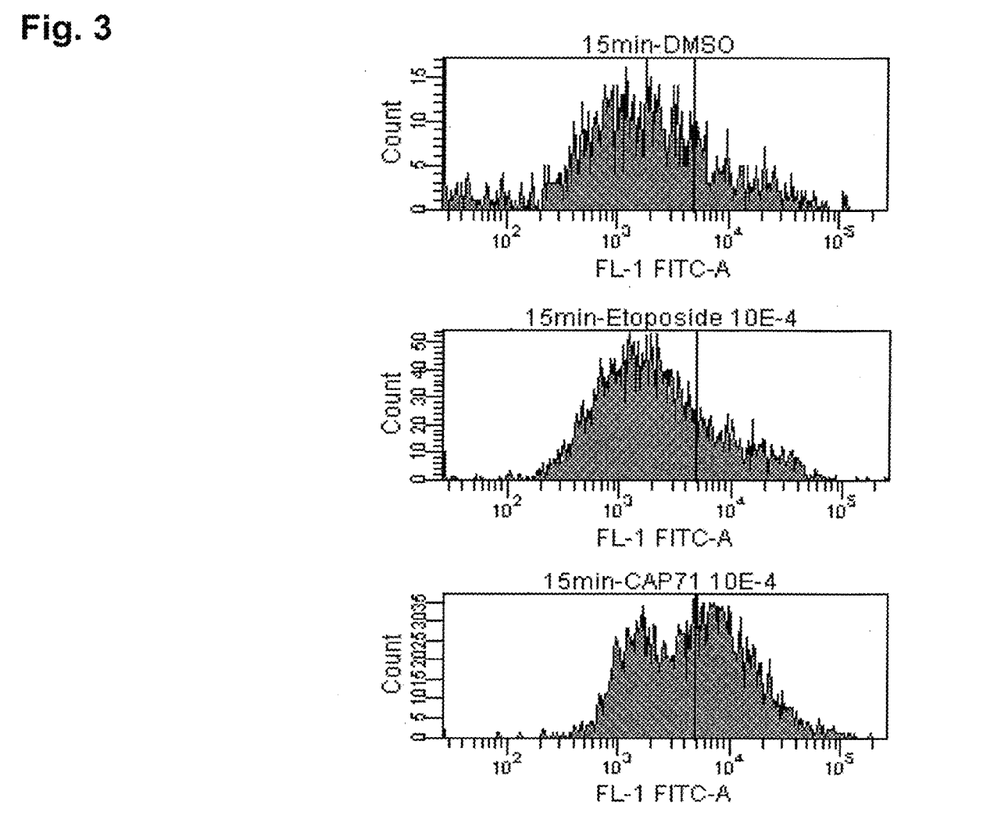
FIG. 3 shows the inhibition of MDR-1 activity in Kelly cells by CAP7.1 in a functional MDR-1 assay.

In FIG. 3, the top diagram shows an intracellular JC-1 signal in the presence of the negative control (DMSO). The intracellular JC-1 signal in the presence of etoposide is identical (middle diagram). In the presence of CAP7.1, the intracellular JC-1 signal is increased (bottom diagram). This intracellular accumulation of JC-1 shows the inhibition of the MDR-1-mediated (P-glycoprotein-mediated) substrate efflux by CAP7.1, but not by etoposide.

Example 4: Effect of CAP7.1 and Etoposide on the Cell Cycle

Multidrug-resistant U937 cells grown in RPMI medium were washed and resuspended at a concentration of $10^6$ cells/ml in PBS containing $10^{-4}$ mol/l CAP7.1, $10^{-4}$ mol/l etoposide and 1 µl (0.05%) DMSO, respectively. A control contained no CAP7.1, no etoposide and no DMSO. The cells were incubated for 48 h. After 18 h, 24 h and 48 h of incubation, respectively, cell cycle analysis was performed as follows:

Cells were washed once with CellWash, fixed with fridge-cold 70% Ethanol for 30 min at 4° C. and washed three times. RNA was digested with RNAse A (100 pg/ml in PBS) for 10 min at room temperature. Cells were washed once with CellWash and stained with propidium iodide (50 pg/ml in PBS) for 5 min at room temperature in the dark. Cells were analyzed immediately by flow cytometry using a FACScanto II apparatus.

Figure 4:
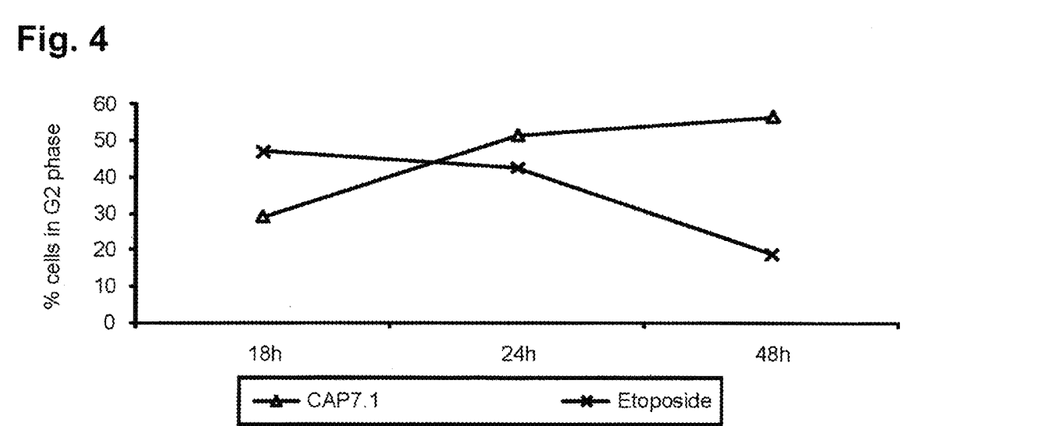
FIG. 4 shows the effect of CAP7.1 and etoposide on the cell cycle in U937 cells.

The percentage of cells in G2 phase is shown in FIG. 4. With increasing incubation times, etoposide (X symbols) leads to a reduction in the fraction of cells in G2 phase, whereas CAP7.1 (triangle symbols) leads to an increase in the fraction of cells in G2 phase. This is indicative of a delayed induction of apoptosis as compared to etoposide.

Example 5: Cytotoxicity of CAP7.1 and of Etoposide on the Cell Line HT-29

HT-29 cells, which are not multidrug-resistant, were grown in DMEM, 10% foetal calf serum, 2 mM glutamine and 100 U/I Pen/Strep medium and then washed. Cells were resuspended at a concentration of $10^6$ cells/ml in medium as described above containing various concentrations of CAP7.1 and etoposide, respectively, ranging from $10^{-10}$ mol/l to $10^{-4}$ mol/l.

Cells were harvested, counted, and inoculated at the appropriate concentration of $10^4$ cells/well (100 µl volume) into 96-well microtiter plates. After 24 h, the drugs were applied to triplicate culture wells, and cultures were incubated for given times at 37° C. XTT was prepared at 1 mg/ml in pre-warmed (37° C.) medium (RPMI 1640) without serum. PMS was prepared at 5 mmol/l (1.53 mg/ml) in PBS. Fresh XTT and PMS were mixed together at appropriate concentrations. For a 25 µl ηol/l XTT-PMS solution, 25 µl of the 5 mmol/l PMS solution were added per 5 ml of XTT (1 mg/ml). 50 µl of this mixture were added to each well on given time points after cell inoculation. After incubation at 37° C., the plates were mixed on a mechanical plate shaker, and absorbance was measured with an ELISA Reader to determine cell viability.

Figure 5:
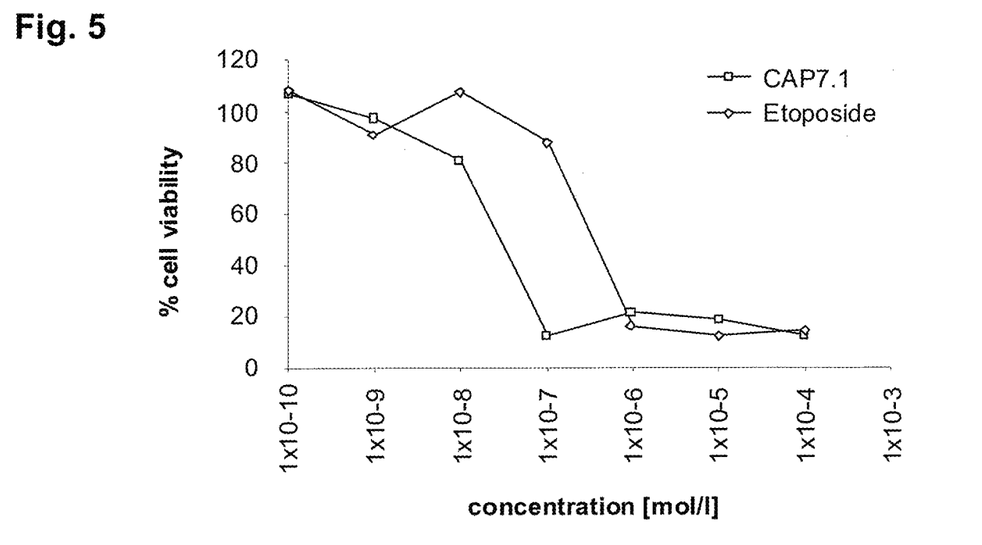
FIG. 5 shows the cytotoxicity of CAP7.1 and of etoposide on the cell line HT-29.

FIG. 5 shows cell viability plotted against the concentrations of CAP7.1 (square symbols) and etoposide (diamond symbols), respectively. The $IC_{50}$ value of CAP7.1 is at a 10-fold lower concentration than the $IC_{50}$ value of etoposide.

Example 6: Expression of CES1 and CES2 in Tumour Cell Lines

Different cell lines responsive to compounds of formula (I) were tested for endogenous Expression of CES1 and CES2. Expression was quantified by real-time PCR.

Cells were harvested, counted, and inoculated at the appropriate concentration of $10^6$ cells/well (2 ml volume) into 6-well plates with drugs for given time points at 37° C. RNA was extracted and cDNA was synthesized with random hexamers and TaqMan reverse transcriptase to be used in real-time PCR in a reaction with PCR buffer mix and specific primers for human CES1 and CES2.

Figure 6:
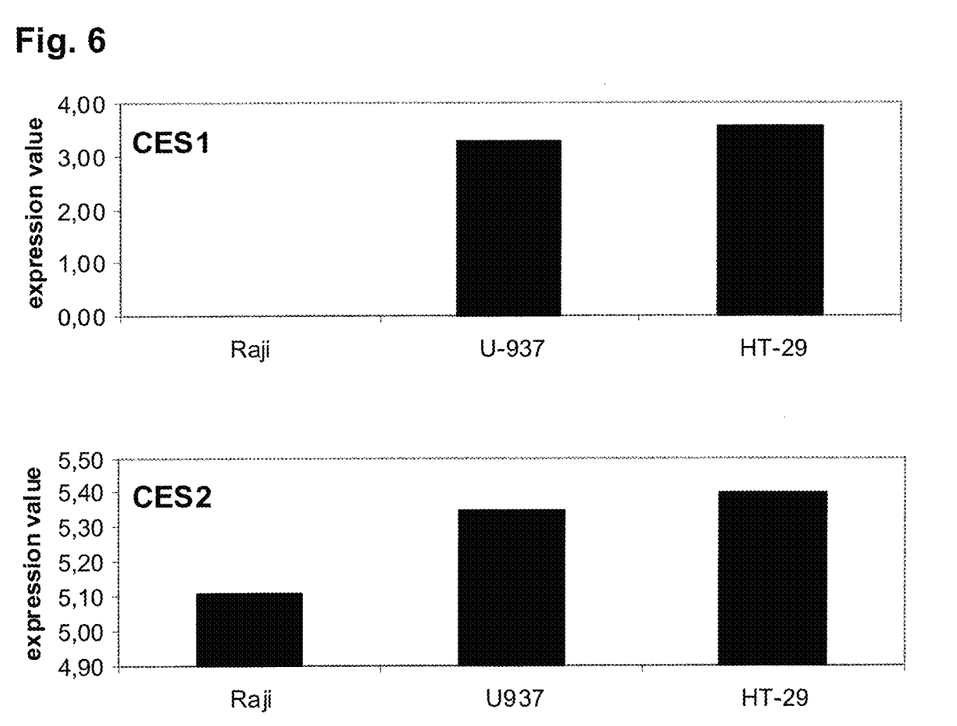
FIG. 6 shows the expression of CES1 and CES2 in tumour cell lines responsive to CAP7.1.

The results for CAP7.1 obtained in the cell lines Raji, U-937 and HT-29 are illustrated in FIG. 6, which shows inverted ACT values.

Raji cells express only CES2. U-937 and HT-29 cells express both CES1 and CES2. Accordingly, these cells respond to treatment with compounds of formula (I), in particular CAP7.1.

Example 7: Effect of CAP7.1 in Animal Studies

The objective of this study was to evaluate the potential modifications of cardiovascular function and cardiac electrophysiology by CAP7.1. The intravenous route was selected, as it is the intended mode of administration in human therapeutic use.

A total of four cynomolgus monkeys (two males and two females) were implanted with telemetric devices and allocated to a single group. They received a single dose of the vehicle (Cremophor/ethanol/NaCl) or CAP7.1, by intravenous 30-minute infusion. Cardiovascular parameters were monitored up to 24 hours following single infusion. The cardiovascular parameters evaluated in this study included heart rate, diastolic, systolic and mean arterial pressure, and duration of the PQ, QRS and QT intervals. CAP7.1 induced no relevant modifications in the cardiac electrophysiological parameters of conscious monkeys. No arrhythmias were observed.

The lack of cross-resistance to CAP7.1 of MDR-mediated etoposide-resistant cell lines in vitro was confirmed in vivo in mice bearing NSX2 tumour xenografts. CAP7.1 administration resulted in a clear inhibition of tumour growth compared to control.

The toxicity profile of CAP7.1 in animals corresponds to that of other topoisomerase II inhibitors and in particular etoposide, i.e. the main toxicity at sublethal dose is bone marrow suppression affecting predominantly neutrophils and red cells. However, animals treated with etoposide experience significant weight loss whereas animals receiving CAP7.1 do not.

Animals receiving CAP7.1 experienced reversible tooth damage in the high dose group.

Animal toxicology studies have shown that the $LD_{10}$ value of CAP7.1 in mice is 120 mg/kg (360 mg/m$^2$) whereas the $LD_{10}$ value reported in the literature for etoposide given to mice is 34 mg/kg (102 mg/m$^2$) after i.v. administration.

Example 8: Clinical Studies

Nine heavily pre-treated patients were recruited to a combined Phase I/I Ia safety/efficacy study. The patients had tumours that were metastatic and/or that reduced the function of at least one organ.

In all patients, the tumours were clinically assessed and the history of their disease was recorded. Tumour markers were determined.

Each of the patients had been treated before with different drugs, which on admission to the study had failed. Thus, the respective tumours were resistant to treatment with the respective drugs (listed under "previous treatment" for the respective patients).

Patient 1: 57 years old, male, squamous cell hypopharynx carcinoma with pulmonary metastases. Previous treatment: cisplatin, pololobe kinase, cisplatin, 5-fluorouracil, panitumumab.

Patient 2 (non-responder after two cycles of treatment): 49 years old, squamous cell oropharynx carcinoma. Previous treatment: cetuximab, cisplatin.

Patient 3: 62 years old, male, sarcomatoid thymus carcinoma with pulmonary metastases, Previous treatment: tyrosine kinase inhibitor, trofosfamide, etoposide, doxorubicin (adriamycin).

Patient 4: 65 years old, female, adenocarcinoma of the gall bladder with lymph node metastases. Previous treatment: cisplatin, gemcitabine.

Patient 5 (non-responder after two cycles of treatment): 65 years old, urothelium carcinoma of urine bladder with liver metastasis. Previous treatment: cisplatin, gemcitabine.

Patient 6: 50 years old, male, cancer of unknown primary origin with small-cell brain metastases. Previous treatment: cisplatin, etoposide.

Patient 7 (non-responder after two cycles of treatment): 64 years old, squamous tonsillar carcinoma with metastases in lymph nodes, liver and lung.

Patient 8: 32 years old, male, mixed seminoma and non-seminoma germ cell carcinoma of the testis with renal, pulmonary, retroperitoneal, hepatic and cerebral metastases.

Patient 9: 67 years old, female, ovarian adenous carcinoma with abdominal metastases.

A cycle of treatment consisted of CAP7.1 administration by infusion on 5 consecutive days, followed by an intermittent period of 16 days in which no CAP7.1 was administered. After completion of such a cycle, the next cycle of treatment was initiated. The first cohort (patients 1-3, 8 cycles in total) received CAP7.1 at a daily dose of 45 mg/m², the second cohort (patients 4-6, 9 cycles in total) at a daily dose of 90 mg/m² and the third cohort (patients 7-9) at a daily dose of 150 mg/m².

Pharmacokinetic evaluations were performed before administration, at 30 min during infusion, and after infusion at 15 min, 45 min, 90 min, 3 h, 6 h, 10 h on day 1, and before administration and 15 min after end of infusion on the remaining days. Pharmacokinetics showed that CAP7.1 was processed to etoposide in a delayed way. The majority of CAP7.1 was converted to etoposide after 45 min of CAP7.1 infusion.

All patients tolerated the therapy well without major adverse reactions. Patients 1 to 6 did not experience toxicity. Thus, a total dose per cycle of CAP7.1 of 450 mg/m² is tolerated without toxicity. This represents a 25% increase over the recommended dose of etoposide in small cell lung cancer.

Patients 1, 3, 4, 6, 8 and 9 showed that treatment with CAP7.1 was successful: a stagnation of the disease after the second cycle of treatment was observed in each case.

Example 9: Clinical Studies for Combination Therapy

CAP7.1 was administered with carboplatin to three children with heavily pre-treated advanced neuroblastoma. Two of these patients had received etoposide previously.

CAP7.1 was administered on day 1 of each cycle starting at 200 mg/m² (the usual dose of etoposide in this regimen) and was escalated in successive cycles to 400, 600 and 800 mg/m²; carboplatin was administered at a dose of 150 mg/m² daily on days 2, 3, 4 and 5. Cycles were repeated every 21 days and a total of 4 cycles were administered in each patient. Toxicity was mainly haematological, grade 1-2 at 200 mg/m² and increased to grade 3-4 in the rest of the cycles, but cycle delay due to toxicity was not necessary.

In two of the three patients there were evidences of tumour shrinkage. Thus these observations provide indirect support of the lack of cross-resistance in humans between CAP7.1 and etoposide. Additionally the study supported the good tolerability of CAP7.1 in patients. The half life in plasma in this study evaluated in one of the children treated was 12-30 minutes with a $C_{max}$ of 3.7 pg/ml.

Example 10: Formulation of CAP7.1

CAP7.1 is formulated as a dry white powder. CAP7.1 is presented in 3 mg strengths as a solution for intravenous infusion. The active ingredient is solubilised in 20 ml polyethoxylated castor oil (e.g. Cremophor EL®) and ethanol (50:50) in glass vials before dilution into sterile sodium chloride (0.9%) for infusion. 1, 2 and 3 mg/ml final solution strengths are provided.

The invention claimed is:
1. A method of treating tumor in a subject in need thereof, wherein said method comprises administering to the subject a compound of formula (I)

wherein
X is selected from the group consisting of O, NH and S,
n is 0, 1 or 2, and
$R^1$ and $R^2$ are independently selected from the group consisting of H, methyl, and ethyl, or together form a group $CR^3R^4$ wherein $R^3$ and $R^4$ are independently selected from the group consisting of H, methyl and ethyl, wherein the tumor is metastatic and/or that reduces an organ function; and, wherein the tumor is resistant to etoposide.

2. The method of claim 1, wherein said method comprises administering to the subject a compound selected from the group consisting of and 3. The method of claim 1, wherein the subject is a human.

4. The method of claim 1, wherein the tumor is resistant to treatment with a therapeutic protein or a chemotherapeutic drug exclusive of the compound of formula (I)

wherein

X is selected from the group consisting of O, NH and S, n is 0, 1 or 2, and $R^1$ and $R^2$ are independently selected from the group consisting of H, methyl, and ethyl, or together form a group $CR^3R^4$ wherein $R^3$ and $R^4$ are independently selected from the group consisting of H, methyl and ethyl.

5. The method of claim 1, wherein the tumor is a solid tumor.

6. The method of claim 5, wherein the tumor is selected from the group consisting of adenocarcinoma, hypopharynx cancer, lung cancer, diffuse large cell lymphoma, Burkitt's lymphoma, Hodgkin lymphoma, Non-Hodgkin lymphoma, histiocytic lymphoma, lymphatic lymphoma, acute T-cell leukemia, pre-B-acute lymphoblastic leukemia, gall bladder cancer, bile duct carcinoma, thymus carcinoma, urothelium carcinoma, testicular cancer, prostate cancer, bladder cancer, brain tumor, AIDS-related Kaposi's sarcoma, Ewing sarcoma, rhabdomyosarcoma, neuroblastoma, ovarian cancer, breast cancer, and unknown primary origin (CUP) syndrome.

7. The method of claim 1, wherein the treatment leads to a stagnation of tumor growth or a remission of the tumor.

8. The method of claim 1, wherein said tumor reduces an organ function.

9. The method of claim 1, wherein the tumor expresses at least one of CES1 and CES2.

10. The method of claim 9, wherein the fraction of CES1 and/or CES2 expressing cells of the tumor is 0.50% or higher.

11. The method of claim 1, further comprising administering to the subject a second therapeutic drug compound.

12. The method of claim 1, wherein the compound of formula (I) is administered to the subject intravenously.

* * * * *